US008829252B2

(12) United States Patent
Davoren et al.

(10) Patent No.: US 8,829,252 B2
(45) Date of Patent: Sep. 9, 2014

(54) SYSTEM FOR ALCOHOL PRODUCTION

(75) Inventors: Dennis Jay Davoren, Baton Rouge, LA (US); Seth McConkie Washburn, Houston, TX (US); James Oliver Meredith, Lymington (GB); Krishnan Sankaranarayanan, Pittstown, NJ (US); Bryan Amrutlal Patel, Arlington, VA (US); Milind Bholanath Ajinkya, Oakton, VA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 89 days.

(21) Appl. No.: 13/809,065

(22) PCT Filed: Jun. 20, 2011

(86) PCT No.: PCT/US2011/041030
§ 371 (c)(1),
(2), (4) Date: Mar. 22, 2013

(87) PCT Pub. No.: WO2012/009102
PCT Pub. Date: Jan. 19, 2012

(65) Prior Publication Data
US 2013/0211153 A1    Aug. 15, 2013

Related U.S. Application Data

(60) Provisional application No. 61/363,390, filed on Jul. 12, 2010.

(51) Int. Cl.
C07C 29/04 (2006.01)
B01J 10/00 (2006.01)
B01J 19/00 (2006.01)
B01J 19/24 (2006.01)
B01J 4/00 (2006.01)
C07C 29/06 (2006.01)

(52) U.S. Cl.
CPC ............... *B01J 19/006* (2013.01); *C07C 29/04* (2013.01); *B01J 2219/0011* (2013.01); *B01J 2219/00774* (2013.01); *B01J 10/002* (2013.01); *B01J 19/24* (2013.01); *B01J 4/002* (2013.01); *C07C 29/06* (2013.01)
USPC ......................................... 568/895

(58) Field of Classification Search
CPC ........ C07C 29/06; C07C 29/04; C07C 31/10; B01J 19/006; B01J 19/24; B01J 10/002; B01J 2219/0011; B01J 2219/00774; B01J 4/002
USPC .......................................... 568/895; 422/187
See application file for complete search history.

(56) References Cited

U.S. PATENT DOCUMENTS

| | | | |
|---|---|---|---|
| 2,109,004 A | 2/1938 | Archibald et al. | |
| 2,474,569 A | 6/1949 | Bannon | |
| 3,900,537 A | 8/1975 | Tjutjunnikov et al. | |
| 4,201,628 A | 5/1980 | Church et al. | |
| 4,471,142 A | 9/1984 | Burton et al. | |
| 5,191,129 A | 3/1993 | Irvine | |
| 5,451,349 A | 9/1995 | Kingsley | |
| 5,986,148 A | 11/1999 | Beech, Jr. et al. | |
| 6,906,229 B1 | 6/2005 | Burton | |
| 7,345,139 B2 * | 3/2008 | DeBruin | 528/308.1 |
| 7,481,871 B2 | 1/2009 | Frye et al. | |
| 2009/0270656 A1 | 10/2009 | Fukuoka et al. | |

FOREIGN PATENT DOCUMENTS

| | | |
|---|---|---|
| DE | 1807369 | 10/1970 |
| GB | 705548 | 3/1954 |
| WO | 99/33557 | 7/1999 |

* cited by examiner

*Primary Examiner* — Brandon Fetterolf
*Assistant Examiner* — Blaine G Doletski
(74) *Attorney, Agent, or Firm* — Andrew B. Griffis

(57) ABSTRACT

The invention concerns a system and process for alcohol production.

15 Claims, 4 Drawing Sheets

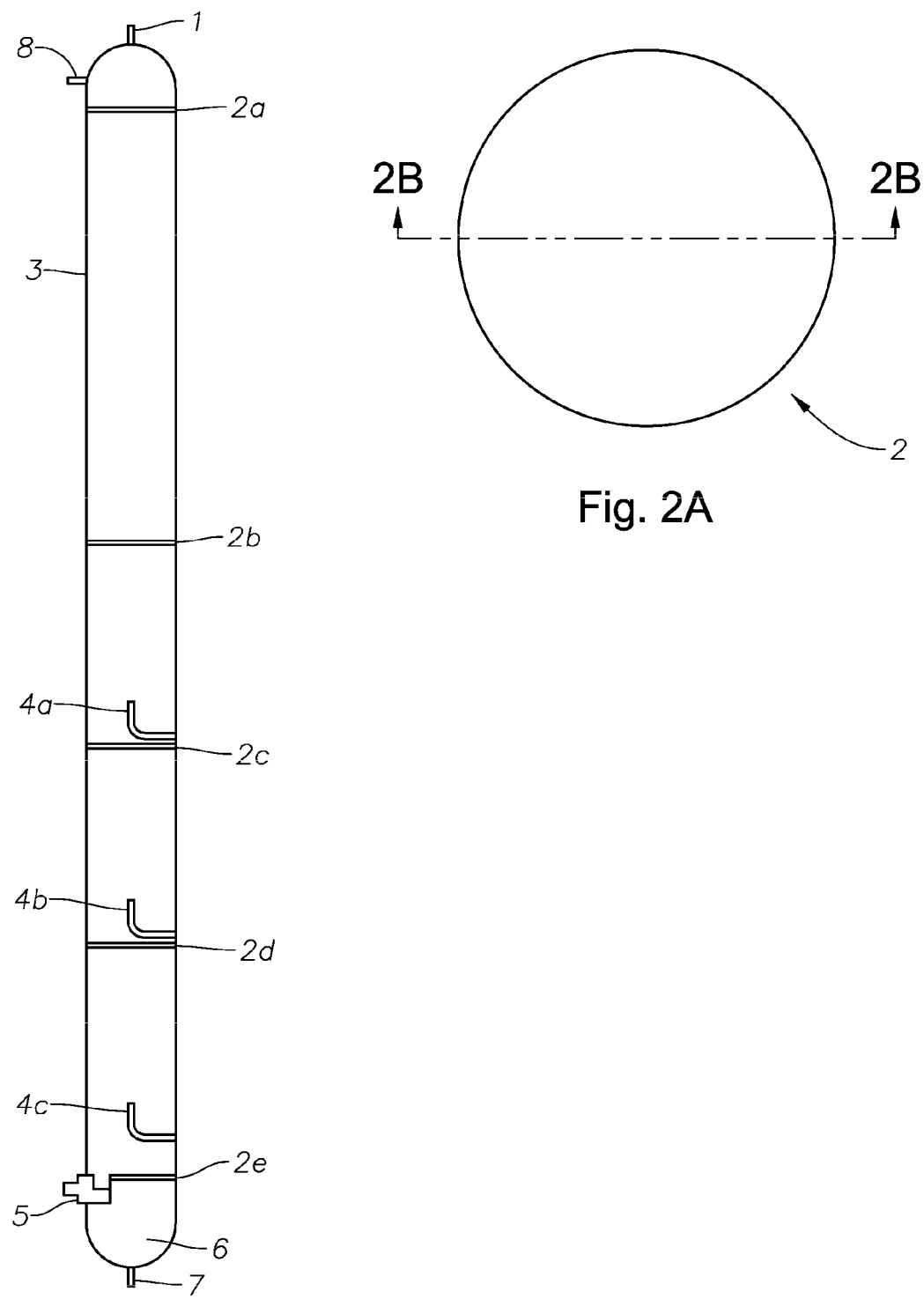

SYSTEM FOR ALCOHOL PRODUCTION

CROSS REFERENCE TO RELATED APPLICATIONS

This application is a National Stage Application of International Application No. PCT/US2011/041030, filed Jun. 20, 2011, which claims priority to Provisional Application No. 61/363,390, filed Jul. 12, 2010, the disclosures of which are incorporated by reference in their entireties.

FIELD OF THE INVENTION

The invention relates to a system for the production of alcohols, particularly isopropyl alcohol ("IPA" or isopropanol).

BACKGROUND OF THE INVENTION

In sulfuric acid catalyzed olefin hydration, olefin is contacted in a mixed phase reactor with sulfuric acid to produce an extract containing alcohol strongly bound to the acid. In a second step, the extract is diluted with water, heated and stripped of the alcohol at low pressure. The acid is returned and recontacted with olefin. This scheme is used, for instance, in the manufacture of IPA from propylene and the manufacture of secondary butyl alcohol (SBA) from butene.

Typically, in the first step, sulfuric acid contacts gaseous propane in a bubble column-type device.

The present inventors have discovered that this type of reactor can suffer from dead zones, with gas preferentially held up behind baffle plates. This can upset the operation of the reactor. In certain cases, such as in the production of IPA, when the IPA rich stage reactor becomes a gas-liquid-liquid reactor, the second phase being isopropyl ether (IPE), the IPE can accumulate behind baffles, destabilizing the operation of the reactor. Accordingly, in an embodiment of the present invention, inverted conical baffles are used.

Conical baffles are per se known in gas-liquid mixing systems. See U.S. Pat. No. 5,451,349.

The present inventors have also found a system having internal configurations which increases the hydrodynamic stability of operation and the reliability of the operation of the IPA-rich stage reactor.

SUMMARY OF THE INVENTION

The invention is directed to a system for the production of alcohols, particularly IPA and SBA. The invention is also directed to an apparatus which can reduce the accumulation of gas and the presence of a second liquid phase.

In an embodiment the invention concerns the use of conical baffles in a distillation apparatus.

The present inventors have also discovered a system having internal configurations which increases the hydrodynamic stability of operation and the reliability of the operation of the IPA-rich stage reactor.

In addition, the invention concerns increasing the capacity of the rich-stage loops system by changing the feed split ratio.

It is an object of the invention to avoid accumulation of IPE in the rich stage reactor used in the production of IPA.

It is another object of the invention to simplify optimization of olefin conversion by optimization of the rich stage loops.

These and other objects, features, and advantages will become apparent as reference is made to the following detailed description, preferred embodiments, examples, drawings, and appended claims.

BRIEF DESCRIPTION OF THE DRAWINGS

In the accompanying drawings, in certain cases, as noted herein, like reference numerals are used to denote like parts throughout more than one view.

FIG. 1 is an embodiment of a distillation apparatus according to the present invention.

FIGS. 2A and 2B are perspectives of an embodiment of a conical baffle according to the present invention.

DETAILED DESCRIPTION

According to the invention, there is a system for the production of alcohols from olefins, including a rich stage reactor having plural rich stage loops, the improvement comprising the use of inverted conical baffles in the rich stage reactor. The alcohol-containing product ("extract") exiting as bottoms from the rich stage reactor is passed downstream to "second stage" operations wherein the alcohol is recovered. Propylene exiting as overheads from the rich stage reactor are typically sent to a lean stage reactor wherein addition propylene is converted to IPA. The second stage and lean stage do not per se form a part of the present invention.

The invention is better understood by reference to the several figures, which are intended to be representative of embodiments of the invention and not restrictive thereof. Accordingly, many variations will suggest themselves to one of ordinary skill in the art.

In FIG. 1, plural nozzles 4a, 4b, 4c provide inlets for propylene entering the column through wall 3. The nozzles are preferably jet nozzles per se known in the art, wherein feed exits at a very high velocity and preferably impinges on the baffles. This creates very well mixed zones in the reactor. Optional additional mechanical mixing or agitation devices may be used, as would be readily apparent to one of skill in the art in possession of the present disclosure. However, one of the advantages of the present invention is that such mechanical mixing and/or agitation devices are not necessary and in embodiments are not used in the rich stage absorber or distillation column shown in FIG. 1. Outlet 1 allows some propylene and propane to exit the column (typically sent to a lean stage reactor to complete conversion of propylene; again, this aspect of alcohol production is not per se a part of the present invention). Sulfuric acid is introduced through one or more nozzles such as 8, generally above the top baffle 2a and to the side of outlet 1.

Figure 2B:
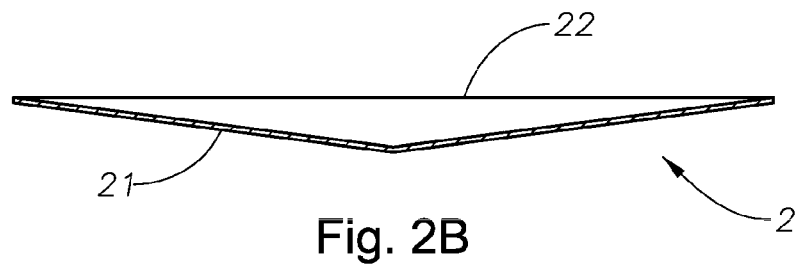

Plural baffles 2a, 2b, 2c, 2d, and 2e perform the function of effectively staging the liquid phase, which leads to superior performance of the reactor. The baffles are preferably conical in shape, as shown in FIG. 2B, discussed in detail below. In the case of conical baffles they should be inverted, as shown in FIG. 2B. In the inverted configuration, meaning that the apex of the conical structure is facing the bottom of the distillation column shown in FIG. 1, the build up of IPE is avoided. Thus, the term "inverted conical baffle" as used herein means a baffle, conical in structure, and inverted so that the apex is facing the bottom of the distillation column. It will be understood by one of skill in the art that in the context of the system described herein the conical baffle does need to be exactly conical but maybe a variation thereon, as described more fully herein.

In order to avoid confusion, it should be understood that a cone is a three-dimensional geometric shape that tapers smoothly from a flat, usually circular base to a point called the apex (or vertex). More precisely, it is the solid figure (although as discussed elsewhere herein, the conical baffle may have perforations) bounded by a plane base and the surface (called the lateral surface) formed by the locus of all straight line segments joining the apex to the perimeter of the base. The structure is generally solid, except where perforated. The axis of a cone is the straight line (if any), passing through the apex, about which the lateral surface has a rotational symmetry. In common usage in elementary geometry, cones are assumed to be right circular, where right means that the axis passes through the center of the base (suitably defined) at right angles to its plane, and circular means that the base is a circle. Contrasted with right cones are oblique cones, in which the axis does not pass perpendicularly through the center of the base. In general, however, the base, according to the present invention, may be any shape, although in embodiments it is circular, and the apex may lie anywhere (though it is often assumed that the base is bounded and has nonzero area, and that the apex lies outside the plane of the base). For example, a pyramid is technically a cone with a polygonal base. In most preferred embodiments the conical baffle is a right circular cone, and the angle between the base and any straight line joining the perimeter of the base to the apex forms an angle of approximately 2 to approximately 6 degrees.

In preferred embodiments the baffles do not cover the entire cross-section of the column and in embodiments cover between 60-90% or 70-80% or 75-85% of the cross-sectional area of the column. Ranges also include any lower percentage listed to any higher percentage listed, e.g., 70-85%. An alternative is where the baffles are perforated, in which case they may extend across the entire cross-sectional area of the column, although it will be understood that the baffles may extend across less than the entire cross-sectional area and also be perforated.

It will be further understood that in embodiments the conical baffle does not need to reach a point at the apex but may in embodiments have an apex that is itself a flat plane or is generally convex downward.

Figure 3:
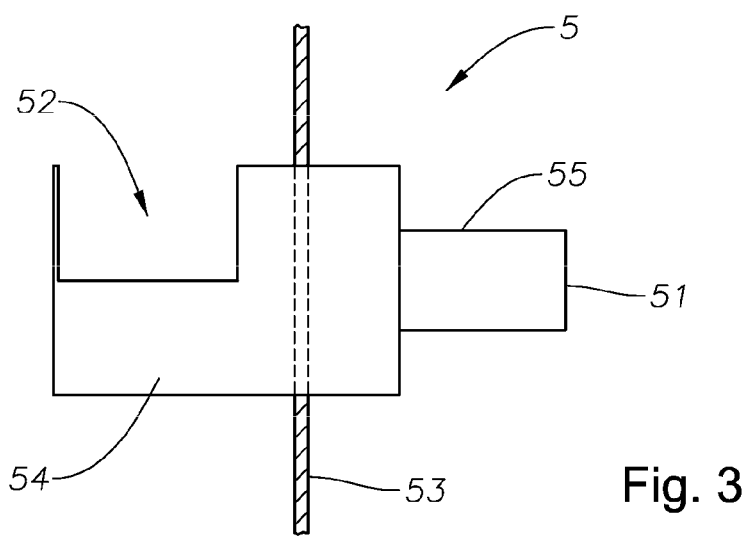
FIGS. 3-4 are perspectives of the de-entrainment device.
Figure 4:
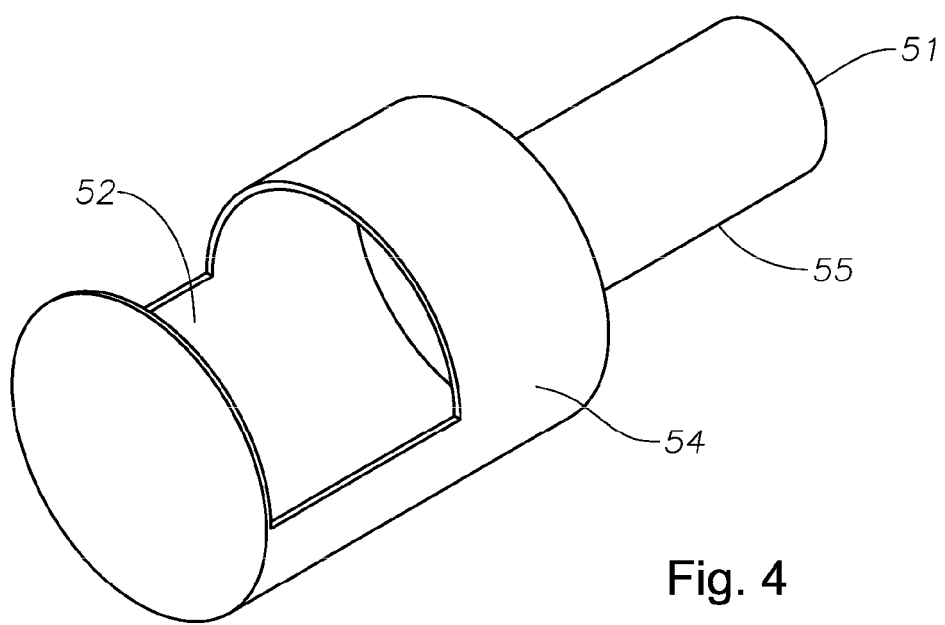
Figure 5:
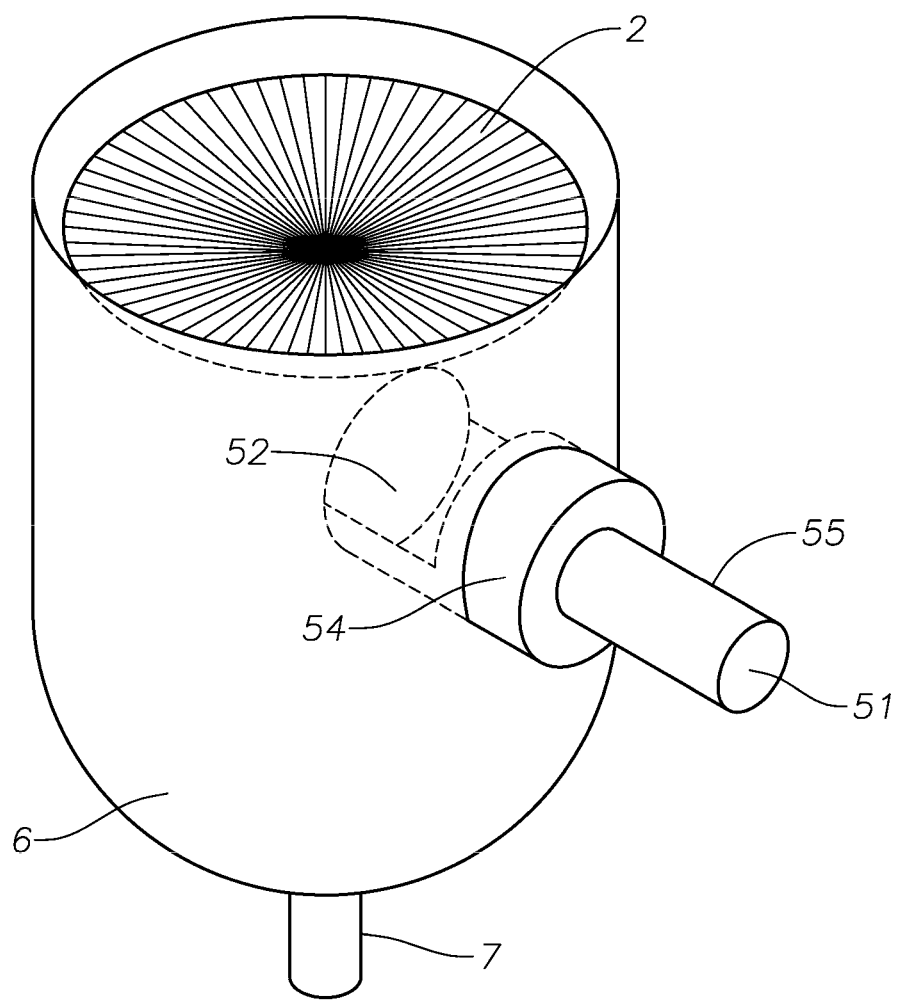
FIG. 5 is a perspective of a bottom portion of a distillation apparatus according to the present invention.

Product is taken off via conduit 7 in the bottoms 6 of the column shown in FIG. 1. De-entrainment device 5, illustrated in more detail in FIGS. 3-5, provides an outlet for sulfuric acid and some gas, from the perspective of the rich stage absorber in the system, or a common inlet for the plural loops, from the perspective of the loops in the system. In alternative embodiments there may be more than one de-entrainment device and it is possible that each loop has a separate de-entrainment device associated with it. Gas-liquid flow preferentially flows down on the side of the reactor opposite from the de-entrainment outlet 5. In this fashion, the gas-liquid mixture flows in a circuitous fashion to reach this outlet and gas-liquid separation is believed to be maximized. This is achieved due to the asymmetry set-up by the flow, as there is a liquid draw on the side of the vessel through de-entrainment device 5 (and thus mechanical stirring or agitation can be avoided).

Note that the inverted conical baffle of the preferred embodiment of the present invention has been determined by experiments by the present inventors to be superior to other baffles, such as a plano-convex baffle, for at least the reason that such a structure avoids of build up of by-products (e.g., IPE in the case of the hydration of propylene) and other conditions which cause reactor upset.

Certain other features associated with the column in FIG. 1 are not shown for convenience of view but would be readily apparent to one of ordinary skill in the art, for example, thermocouples, valves, compressors, heaters, heat exchangers, and the like.

Note that from the perspective of the rich stage absorber in FIG. 1, the plural nozzles represented by 4a, 4b, and 4c are inlets and de-entrainment device 5 is an outlet, but from the perspective of the loops system described further below, e.g., with respect to FIG. 6, the nozzles are outlets and the de-entrainment device is an inlet to the loop system. Thus, usage herein may vary but the meaning should be clear from the context.

FIGS. 2A and 2B show perspectives of baffle 2. Figure A shows a top view and FIG. 2B shows the perspective across line 2B in FIG. 2. The diameter of baffle 2 in FIG. 2A is less than the inner diameter of the column, such as 70-90% of the diameter, as discussed above, and/or the baffle may be perforated, such as with holes located at each of the marks shown on line 21, in which case the diameter of 2 may cover the entire cross section of the column. The baffle forms an inverted pyramid of solid material formed by line 22 and the cone formed by line 21 in preferred embodiments the baffle is not perforated It should be noted that the materials by which the various structures described herein are constructed do not per se form a part of the present invention, but would be principally determined by corrosion considerations as opposed to fluid mechanical considerations. One of ordinary skill in the art would be able to select the materials for and construct/fabricate the apparatus described herein without undue experimentation. Furthermore, it will be understood that the system described herein also has various valves, compressors, conduits, heat exchangers, and the like, associated therewith.

Continuing with the description of the invention, the bottom portion 6 of the column in FIG. 1 comprises baffle 2e, de-entrainment device 5, and product outlet 7. De-entrainment device 5 is shown in detail in FIG. 3 through 5.

A side perspective of the de-entrainment device 5 in FIG. 1 is shown in FIG. 3. Sulfuric acid and some gas de-entrains through opening 52 of de-entrainment device 5, and exits through the reactor wall 53 through conduit 55 and out exit 51. Portion 54, extending through reactor wall 53, is solid.

A second perspective of de-entrainment device is shown in FIG. 4, with like reference numerals used to denote like parts throughout the two views. The sulfuric acid and some gas passes out of the column through opening 52 in walled structure 54, through to conduit 55, having opening 51.

The details of the bottom portion of the rich stage absorber column of FIG. 1 are shown in FIG. 5. As shown, inverted conical baffle 2, extending approximately to 80-90% of the entire cross-section of the column's cross-section is immediately above de-entrainment device 54, having opening gap 52. The solid side portion 54 (extending by dotted lines inside reactor wall 6), conduit 55 and exit port 51 is intended for the sulfuric acid to leave the reactor. The sulfuric acid then goes to the loops system, where additional propylene/propane is added, as discussed in more detail herein, such as with respect to FIG. 6, below. The product IPA exits conduit 7.

As suggested above, the angle and diameter of the inverted conical baffles may vary. Studies were undertaken to identify the optimal design. An angle of between 2 to 6 degrees (for each of the angles represented by line 22 meeting with line 21 in FIG. 2B) is sufficient to virtually eliminate a build-up of the gas phase and IPE phase. Gas-liquid fluxes near the baffles at various elevations are different and accordingly the baffles need not have uniform designs within a given column.

The present invention is also concerned with changing of the feed split ratio, which will be explained below in detail, with reference to FIG. 6.

The capacity increase with changing the feed split ratio is a result of extensive experimentation, including the use of Computational Fluid Dynamics (CFD), and was not intuitive. In the preferred embodiment, there are plural loops, such as three reactor loops 77, 86, and 81, in FIG. 6, into which the feed is injected with the aid of one or more compressors represented by 75a. Thorough mixing occurs in these loops as vapor and liquid move through the conduits, preferably in the bubble flow regime. These plural conduits 77, 86, and 81 are fed by line 80 with the aid of compressor 75a from conduit 74 supplying feed from propylene feed drum 73, which in turn is fed from line 71 from multiple possible sources. Line 72 represents supply conduit of IPE recycle. In a preferred embodiment, two of those loops 81 (shown with heat exchanger 76b and conduit 87 connecting to nozzle 82b) and 86 enter the bottom section of the rich stage absorber 700 (by way of specific example, via jet nozzles 4b and 4c in FIG. 1) and the other loop 77 enters a section of column 700 through nozzle 82a (after passing through heat exchanger 76a), above the bottom that is separated by a baffle 200 (by way of specific example, via jet nozzle 4a in FIG. 1).

Figure 6:
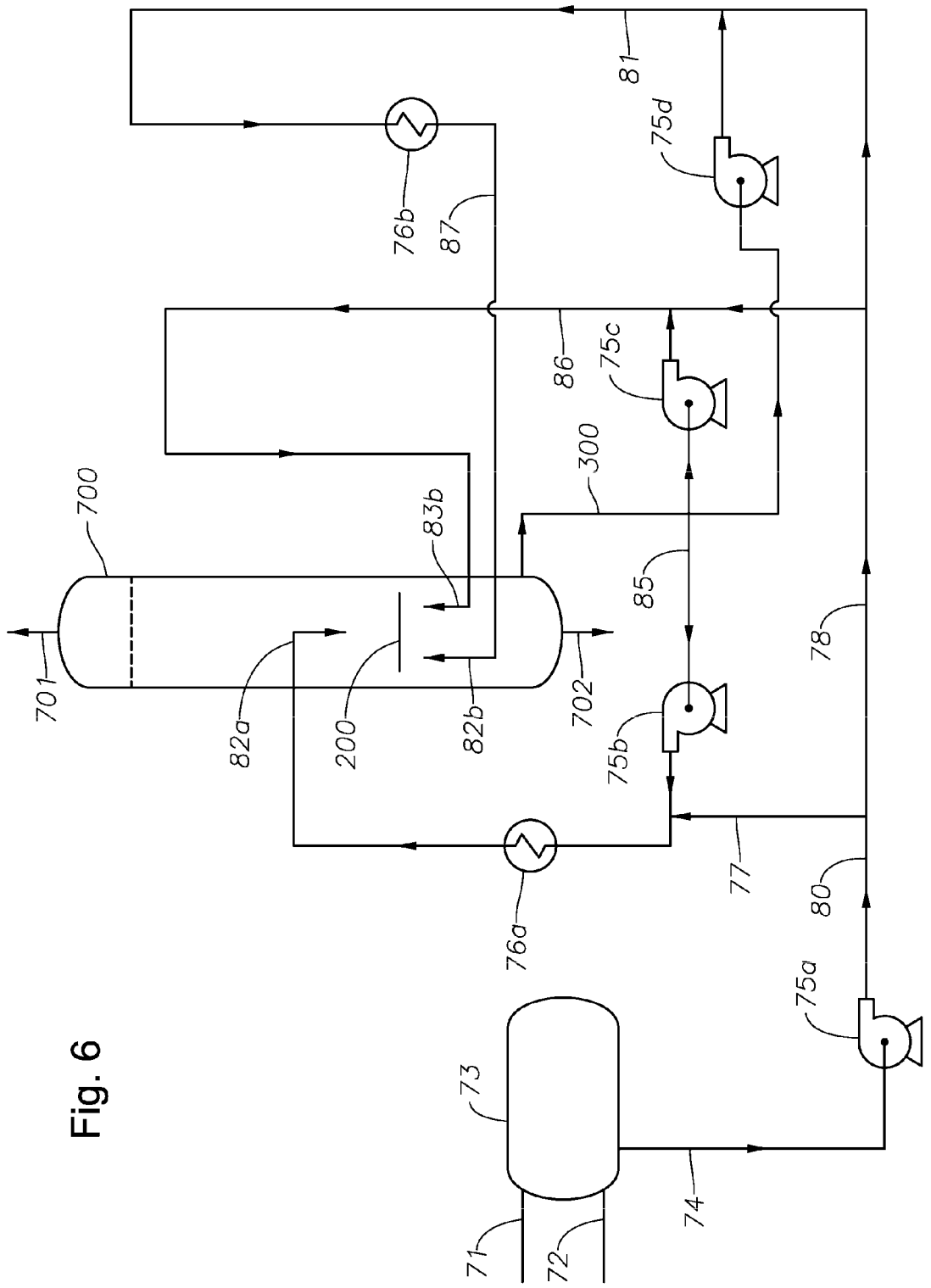
FIG. 6 is a block diagram of an embodiment of the system comprising the rich-stage reactor with associated loops.

Sulfuric acid leaving de-entrainment device (5 in FIG. 1), not shown with specificity in FIG. 6, leaves vessel 700 via conduit 300 and is recycled back into the system through compressors 75b, 75c, and 75d, dispersed amongst the loops at the intersection of conduit 300 (crossing over through compressor 75d to line 81), conduit 85, and the line passing through compressor 75c to line 86. Various other conduits which may be used to recycle the sulfuric acid are not shown for convenience of view.

In this manner, sulfuric acid is drawn into the reactor loops from the rich stage absorber and mixed with the propylene injected also into the loops. The propylene and acid mix and react in the loops as they flow through and then exit into the rich stage absorber 700 in FIG. 6. Unreacted propylene along with propane passes out of the system through overhead vent or outlet 701 and product comprising IPA passes out of the system through bottoms vent or outlet 702. The disposition of the overheads and bottoms have been briefly described above and, again, do not per se form a part of the invention.

The two-phase jets injecting feed at 82a, 82b, and 83b in FIG. 6 can be oriented either in an upward or downward fashion. Upward pointing jets, as shown in FIGS. 1, 4a, 4b, and 4c, are preferred.

It is to be understood that the entire system or parts thereof may be operated partially or entirely by computer control, such as feedback/feed forward control described in PCT/US2010/033088.

Given specific overall propylene feed rate; the feed can be split between the three loops independently. Historically, the feed has been basically split based on the volume of the reactor loop it was entering. After that, there was some optimization based on the observed temperatures in the reactor loop exit, which is a rough indication of how much propylene reacted in the loop. Prior to the present invention, the thinking was to maximize the amount of propylene that converts in the reactor loops before it enters the rich stage absorber (vessel 700 in FIG. 6 or the column shown in FIG. 1) by making small adjusting in the feed ratio and keeping the burden equal on three loops. The relationship amongst the loops is very complex and optimization of the feed split ratio was heretofore considered entirely an art as opposed to a science.

The present inventors have determined that there are three things needed to get good conversion—high temperatures, good mixing, and low concentration of reaction products in the acid feed to the loops, the acid feed being provided by de-entrainment device 5 in FIG. 1, or line 300 in FIG. 6.

Given that the acid feed to all three loops comes from the de-entrainment device, there isn't much that can be changed to affect that factor. Accordingly, given a single de-entrainment device, this simplifies the problem.

In respect to temperature, the propylene enters the loop system as a liquid (in the specific embodiment of FIG. 6, through line 74 through compressor 75a to line 80, whence it splits to lines 77 and 78, the latter splitting to lines 86 and 81) and then flashes, which cools down the loops greatly. The loop temperatures then start to increase as the propylene exothermically reacts. The more propylene is added, the colder the loops become and the incremental conversion in the loops decrease. This means the rich stage absorber itself must convert more and it gets hotter. This is an issue because there is a temperature limit on the absorber that is based on material integrity. Currently, operations try to target a set reactor loop outlet temperature that is based solely on experience.

Simply adding more propylene is not a solution, because the system begins to convert to slug and then annular flow the more the propylene vaporizes. This decreases the amount of mixing that occurs between the two phases. Through the use of complex computer modeling, overall loop conversions may be predicted from given input properties (flowrate, temperature, composition) of the extract and fresh propylene feeds to each of the loops. The model assumes immediate and complete vaporization of the fresh propylene feed upon its injection into the loops and negligible heat loss from the loops to the environment. Vapor entrainment in the column extract to the loops (0.8 to 1.0 wt %) is also accounted for using data from the simulations. Various preferred embodiments have been determined from this simulation.

In one embodiment, the loops associated with heat exchangers 76a and 76b in FIG. 6 are incorporated by setting a target cooling temperature and then calculating the required heat exchanger duty to reach that temperature. The target cooling temperatures are set to 215° F. (approximately 102° C.) in the loop passing through heat exchanger 76a, and 220° F. (about 105° C.) in the loop passing through heat exchanger 76b. Though the simulations can predict the relative temperature change in the loop after propylene injection, the total value of the temperature is sometimes offset because of inaccuracies in propylene's heat of vaporization. It is known that estimates of propylene's heat of vaporization from loop thermocouple measurements vary considerably over time. Accordingly, the present inventors took an average value of the heat of vaporization was used as an approximation in the simulations. The net effect is that the heat exchanger duties may under or over-predict the required duty.

At this point, it is useful to recognize the gross configuration of the reactor. The rich stage reactor 700 in FIG. 6, is essentially a counter-current gas-liquid absorber. The ideal configuration for these are counter-current plug flow from reaction engineering theory. Reactor engineering practice predicts that a simple bubble column will have a gas phase which is essentially in plug flow (which is desirable), and a liquid phase which is well-mixed (less desirable). The amount of back mixing in the liquid phase, therefore, will be too high for a simple bubble column reactor. Staging of reactor will lead to staging of the liquid phase, which will positively impact the gross hydrodynamics in a positive fashion, i.e., lead to more plug flow type behavior of the liquid phase.

Reaction engineering theory predicts that a configuration with a fixed volume will have higher conversion and absorption if that volume is portioned into three rather than two stages. Three stages will also lead to a more even distribution of energy dissipation, and will lead to a more favorable gas-liquid interfacial area.

The fraction of fresh propylene added to each of the reactor loops can be varied and tested to determine the optimal feed split. In embodiments, the other operating conditions are fixed, such as the split of extract into each of the loops and the total amount of fresh propylene added. In the case of the three loop system as shown in FIG. 6, the operating split fraction is 10-30% by volume propylene to the loop entering through nozzle 82a, 1-30% by volume propylene to the loop entering through nozzle one of nozzles 82b or 83b, and the remainder entering through the remaining nozzle. Essentially, it has been found that the key is to optimize two of the loops and have the remaining loop be "sacrificial", in that it is essentially not optimized by handles the remaining amount of propylene added to the entire system. Likewise, in a four loop system, three of the loops will be optimized and the fourth will be the sacrificial loop.

While the illustrative embodiments of the invention have been described with particularity, it will be understood that various other modifications will be apparent to and can be readily made by those skilled in the art without departing from the spirit and scope of the invention.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. A system for acid catalyzed hydration of at least one olefin to at least one alcohol, said system comprising a rich stage absorber distillation column in combination with plural reactor loops fluidly connected with said rich stage absorber and wherein said olefin is contacted in a mixed phase with said acid to produce an extract, the improvement comprising the use of plural inverted conical baffles in said rich stage absorber distillation column.

2. The system according to claim 1, wherein said acid is sulfuric acid, said olefin is propylene, and said alcohol is isopropyl alcohol (IPA).

3. The system according to claim 1, wherein said acid is sulfuric acid, said olefin is butene, and said alcohol is secondary-butyl alcohol (SBA).

4. The system according to claim 1, wherein said rich stage absorber is defined by a top portion, a middle portion, and a bottom portion, the top portion including an inlet for said acid and an outlet for gaseous olefin, the middle portion including said plural inverted conical baffles, and the bottom portion including at least one de-entrainment device for de-entrainment of sulfuric acid from said rich stage absorber into said plural reactor loops and an outlet for extract, wherein said at least one de-entrainment device provides a fluid connection between said rich stage absorber and each of said plural reactor loops, and wherein each of said plural reactor loops is also fluidly connected with said middle portion of said rich stage absorber.

5. The system according to claim 4, comprising a single de-entrainment device fluidly connected to each of said plural reactor loops and a separate fluid connection for each of said plural reactor loops with said rich stage absorber.

6. The system according to claim 5, including a reservoir comprising olefin, said reservoir fluidly connected with each of said plural reactor loops.

7. The system according to claim 1, including at least one de-entrainment device passing through the wall of said rich stage absorber, said de-entrainment device substantially according to at least one of FIGS. 3-5.

8. The system according to claim 1, wherein each of said plural inverted conical baffles is defined by a base substantially perpendicular with the vertical walls of said rich stage absorber and wherein the angle of any line drawn from at least one point at the end of said base to the apex of said inverted conical baffle is between about 2 to 6 degrees.

9. The system according to claim 8, wherein the angle of each line drawn from any point at the end of said base to the apex of said inverted conical baffle is between about 2 to 6 degrees.

10. The system according to claim 1, wherein at least one of said conical baffles is perforated.

11. A process for acid catalyzed hydration of at least one olefin to at least one alcohol in a system comprising a rich stage absorber in combination with plural reactor loops fluidly connected with said rich stage absorber and wherein said olefin is contacted in a mixed phase with said acid to produce an extract, wherein fresh olefin is provided to said system by apportionment between said plural reactor loops, the improvement comprising optimizing fresh olefin feed to all but one of said plural reactor loops with respect to olefin conversion of said system, wherein the determination of optimization of olefin conversion is by a predetermined method, and then providing the remainder of said fresh olefin feed to the remaining reactor loop.

12. The process according to claim 11, wherein said system is according to claim 1.

13. The process according to claim 11, said system consisting of three reactor loops fluidly connected at a common point with said rich stage absorber, whereby sulfuric acid enters each of said three reactor loops, and wherein each of said three reactor loops re-enters said rich stage absorber independently and above said common point, and wherein fresh olefin is provided separately to each of said three reactor loops, and wherein two of said loops independently comprises from 15-30 vol % of the total amount of olefin contained in the three loops and rich stage absorber, and the third loop comprises the remainder of olefin contained in the three loops and rich stage absorber.

14. The process according to claim 11, wherein said predetermined method includes holding said rich stage absorber to a predetermined temperature, as measured by a thermocouple contained with said rich stage absorber and calculating the conversion of olefin by temperature difference within each of said plural reactor loops over independently selected distance within each of said reactor loops.

15. The process according to claim 11, wherein the olefin is selected from at least one of propylene and butene and the acid is sulfuric acid.

* * * * *